United States Patent
Lee et al.

(10) Patent No.: US 9,133,267 B2
(45) Date of Patent: Sep. 15, 2015

(54) ANTIBODY TREATMENT OF ALZHEIMER'S AND RELATED DISEASES

(75) Inventors: Virginia Man-Yee Lee, Philadelphia, PA (US); Edward Lee, Philadelphia, PA (US); John Q. Trojanowski, Philadelphia, PA (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 1571 days.

(21) Appl. No.: 12/085,427

(22) PCT Filed: Nov. 21, 2006

(86) PCT No.: PCT/US2006/045145
§ 371 (c)(1),
(2), (4) Date: Apr. 14, 2010

(87) PCT Pub. No.: WO2007/062088
PCT Pub. Date: May 31, 2007

(65) Prior Publication Data
US 2010/0209417 A1 Aug. 19, 2010

Related U.S. Application Data

(60) Provisional application No. 60/738,784, filed on Nov. 22, 2005.

(51) Int. Cl.
| A61K 39/395 | (2006.01) |
| C07K 16/18 | (2006.01) |
| G01N 33/577 | (2006.01) |
| G01N 33/53 | (2006.01) |

(52) U.S. Cl.
CPC ............ *C07K 16/18* (2013.01); *A61K 39/3955* (2013.01); *G01N 33/53* (2013.01)

(58) Field of Classification Search
CPC ... C07K 16/18; A61K 39/395; A61K 39/3955
See application file for complete search history.

(56) References Cited

U.S. PATENT DOCUMENTS

| 6,004,940 | A | 12/1999 | Marasco | |
| 6,180,370 | B1 | 1/2001 | Queen | |
| 6,787,637 | B1 * | 9/2004 | Schenk | 530/387.1 |
| 6,913,745 | B1 | 7/2005 | Schenk | |
| 7,491,530 | B2 | 2/2009 | Dessain | |
| 2003/0068316 | A1 | 4/2003 | Klein | |
| 2005/0129695 | A1 | 6/2005 | Mercken | |
| 2006/0228349 | A1 * | 10/2006 | Acton et al. | 424/133.1 |

FOREIGN PATENT DOCUMENTS

WO WO 92/22653 12/1992

OTHER PUBLICATIONS

Lee EB, Doms RW, Trojanowski JQ, Abel T, Lee VMY. Targeting soluble Abeta oligomers in vivo by passive immunization with a novel conformation selective monoclonal antibody. Society for Neuroscience Abstracts, Annual Meeting, Nov. 2003, Presentation No. 133.7.*
Lee EB et al. Targeting amyloid-beta peptide (Abeta) oligomers by passive immunization with a conformation-selective monoclonal antibody improves learning and memory in Abeta precursor protein (APP) transgenic mice. J Biol Chem. Feb. 2006; 281(7):4292-99.*
Dodel R et al. (2011) Naturally occurring autoantibodies against beta-amyloid: investigating their role in transgenic animal and in vitro models of Alzheimer's disease. J. Neuroscience, 31(15):5847-5854.*
Geylis V et al. (May 2005) Human monoclonal antibodies against amyloid-beta from healthy adults. Neurobiol. Aging, 26:597-606.*
Miller DL et al. (2003) Humoral immune response to fibrillar beta-amyloid peptide. Biochemistry, 42:11682-11692.*
Bird et al. "Single-Chain Antigen-Binding Proteins," Science Reports 242:423-426 (1988).
Braak et al. "Neuropathological stageing of Alzheimer-related changes," Acta Neuropathologica 82:239-259 (1991).
Burton et al. "Human Antibodies from Combinatorial Libraries," Advances in Immunology 57:191-280 (1994).
Gu et al. "Construction and Expression of Mouse-Human Chimeric Antibody SZ-51 Specific for Activated Platelet P-selectin," Thrombosis and Haemostasis 77(4):755-759 (1997).
Hsiao et al. "Correlative Memory Deficits, AB Elevation, and Amyloid Plaques in Transgenic Mice," Science 274:99-102 (1996).
Norris et al. "Effects of Oxidative and Nitrative Challenges on a-Synuclein Fibrillogenesis Involve Distinct Mechanisms of . . . ," J. Bio. Chem. 278(29):27230-27240 (2003).
Walsh et al. "Naturally secreted oligomers of amyloid B protein potently inhibit hippocampal long-term potentiation in vivo," Nature 416:535-539 (2002).
Wright et al. "Genetically Engineered Antibodies: Progress and Prospects," Critical Reviews in Immunology 12(3,4):125-168 (1992).
Barbas et al. "Synthetic human antibodies," Nature Medicine 1 (8):837-839 (1995).
Bard et al. "Peripherally administered antibodies against amyloid B-peptide enter the central nervous system and reduce pathology in . . . ," Nature Medicine 6(8): 916-919 (2000).
Beerli et al. "Inhibition of signaling from Type 1 receptor tyrosine kinases via intracellular expression of single . . . ," Breast Cancer Research and Treatment 38:11-17 (1996).
De Kruif et al. "Selection and Application of Human Single Chain Fv Antibody FRagments from a Semi-synthetic Phage Antibody Display . . . ," J. Mol. Biol. 248:97-105 (1995).
Demattos et al. "Peripheral anti-AB antibody alters CNS and plasma AB clearance and decreases brain AB burden in a mouse model of . . . ," PNAS 98(15):8850-8855 (2001).
Dodart et al. "Immunization reverses memory deficits without reducing brain AB burden in Alzheimer's disease model," 5(5):452-457 (2002).
Flood et al. "FAD mutant PS-1 gene-targeted mice: Increased AB42 and AB deposition without APP overproduction," Neurobiology of Aging 23:335-348 (2002).
Forman et al. "Differential Effects of the Swedish Mutant Amyloid Precursor Protein on B-Amyloid Accumulation and Secretion . . . ," J. Biol. Chem. 272(51):32247-32253 (1997).

(Continued)

*Primary Examiner* — Kimberly A Ballard
(74) *Attorney, Agent, or Firm* — Saul Ewing LLP; Kathryn Doyle; Domingos J. Silva

(57) ABSTRACT

Provided is an antibody that selectively binds to an epitope formed by residues 1-11 of Aβ in an Aβ oligomer, a method comprising using the antibody to treat a disease characterized by such an Aβ amyloid deposit in a patient, and kits comprising same.

18 Claims, 10 Drawing Sheets

(56) References Cited

OTHER PUBLICATIONS

Gong et al. "Alzheimer's disease-affected brain: Presence of oligomeric AB ligands (ADDLs) suggests a molecular basis for reversible . . . ," PNAS 100(18):10417-10422 (2003).

Haass et al. "Take five—BACE and the γ-secretase quartet conduct Alzheimer's amyloid B-peptide generation," The EMBO Journal 23(3):483-488 (2004).

Hartley et al. "Protofibrillar Intermediates of AMyloid B-Protein Induce Acute Electrophysiological Changes and Progressive . . . ," J. Neurosci. 19(20):8876-8884 (1999).

Hartman et al. "Treatment with an Amyloid-B Antibody Ameliorates Plaque Load, Learning Deficits, and Hippocampal Long-Term . . . ," J. Neurosci. 25(26):6213-6220 (2005).

Huston et al. "Protein engineering of antibody binding sites: REcovery of specific activity in an anti-digoxin single-chain Fv . . . ," PNAS 85:5879-5883 (1998).

Hsia et al. "Plaque-independent disruption of neural circuits in Alzheimer's disease mouse models," PNAS 96:3228-3233 (1999).

Janus et al. "AB peptide immunization reduces behavioural impairment and plaques in a model of Alzheimer's disease," Nature 408:979-982 (2000).

Kotilinek et al.."Reversible Memory Loss in a Mouse Transgenic Model of Alzheimer's Disease," J. Neurosci. 22(15):6331-6335 (2002).

Lambert et al. "Vaccination with soluble AB oligomers generates toxicity-neutralizing antibodies," J. Neurochem. 79:565-605 (2001).

Lambert et al. "Diffusible, nonfibrillar ligands derived from AB1-42 are potent central nervous system neurotoxins," PNAS 95:6448-6453 (1998).

Lee et al. "Secretion and Intracellular Generation of Truncated AB in B-site Amyloid-B Precursor Protein-cleaving Enzyme Expressing . . . ," J. Biol. Chem. 278(7)4458-4466 (2003).

Lee et el. "Targetinc Amyloid-B Peptide (AB) Oligomers by Passive Immunization with a Conformation-selective Monoclonal Antibody . . . ," J. Biol. Chem. 281(7):4292-4299 (2006).

Lee et al. "Meningoencephalitis associated with passive immunization of a transgenic murine model of Alzheimer's amyloidosis," FEBS Letters 579:2564-2568 (2005).

Liljestrom et al. "A new generation of animal cell expression vectors based on the Semliki Forest virus replicon," Biotechnology 9:1356-1361 (1991).

Lue et al. "Soluble Amyloid B Peptide Concentration as a Predictor of Synaptic Change in Alzheimer's Disease," Am. J. Pathol. 155(3):853-862 (1999).

Marks et al. "By-passing Immunization: Human Antibodies from V-gene Libraries Displayed on Phage," J. Mol. Biol. 222:581-597 (1991).

McLean et al. "Soluble Pool of AB Amyloid as a Determinant of Severity of Neurodegeneration in Alzheimer's Disease," Annals of Neurology 46(6):860-866 (1999).

Morgan et al. "AB peptide vaccination prevents memory loss in an animal model of Alzheimer's disease," Nature 408:982-985 (2000).

Mucke et al. "High Level Neuronal Expression of AB1-42 in Aild-Type Human Amyloid Protein Precursor. Transgenic Mice: . . . ," J. Neurosci. 20(11):4050-4058 (2000).

Naslund et al. "Correlation Between Elevated Levels of AMyloid B-Peptide in the Brain and Cognitive Decline," JAMA 283(12):1571-1577 (2000).

Nicoll et al. "Neuropathology of human Alzheimer disease after immunization with amyloid-B pepide: a case report," Nature Medicine 9(4):448-452 (2003).

Orgogozo et al. "Subacute meningoencephalitis in a subset of patients with AD after AB42 immunization," Neurology 61:46-54 (2003).

Schenk et al. "Immunization with amyloid-B attenuates Alzheimer-disease-like pathology in the PDAPP mouse," Nature 400:173-177 (1999).

Siman et al. "Presinilin-1 P264L Knock-In Mutation: Differential Effects on AB Production, Amyloid Deposition, and Neuronal . . . ," J. Neurosci. 20(23):8717-8726 (2000).

Trojanowski et al. "Distribution of Tau Proteins in the Normal Human Central and Peripheral Nervous System," J. Histochem. and Cytochem. 17(2):209-215 (1989).

Tuszynski et al. "Thrombospondin Promotes Platelet Aggregation," Blood 72(1):109-115 (1988).

Westerman et al. "The Relationship between AB and Memory is in the Tg2576 Mouse Model of Alzeimer's Disease," J. Neurosci. 22(5):1858-1867 (2002).

* cited by examiner

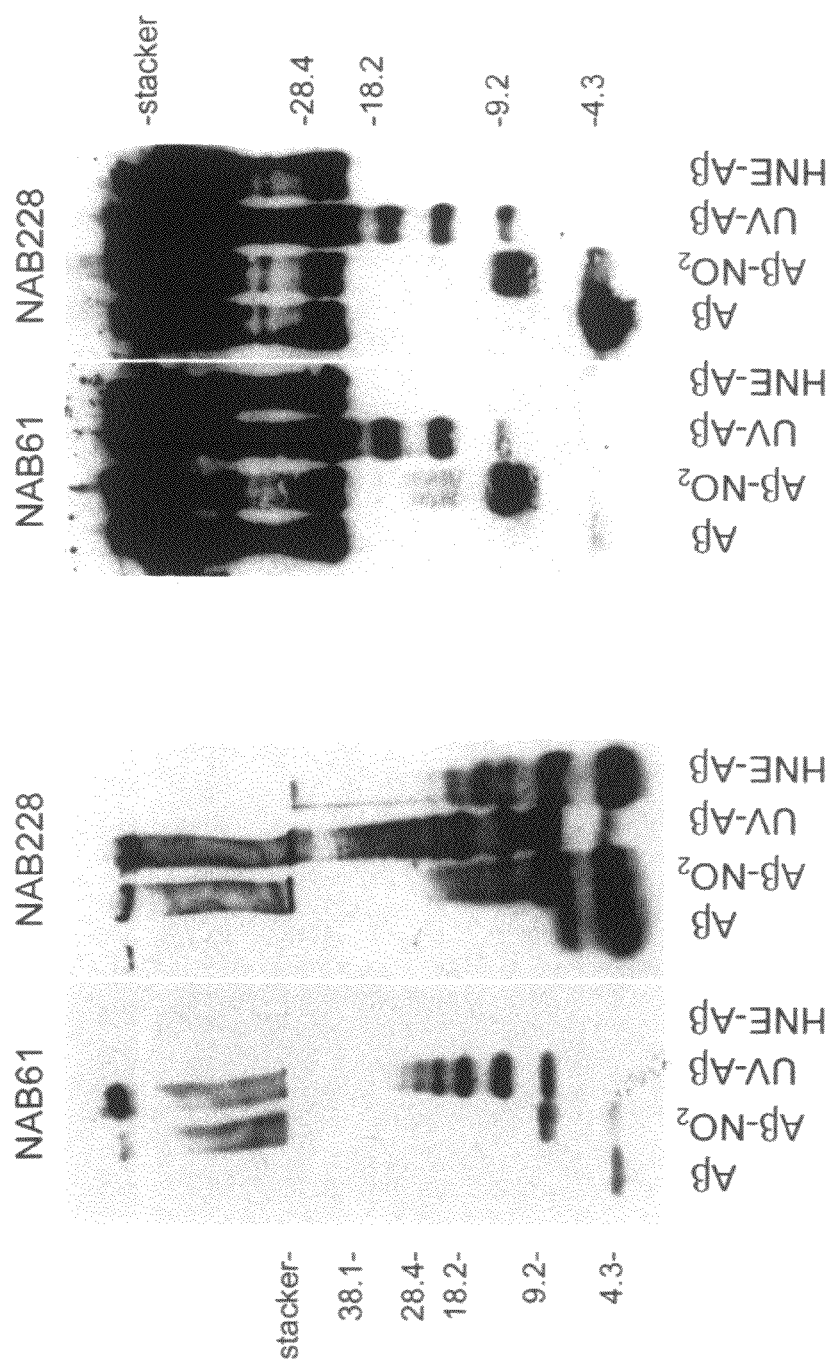

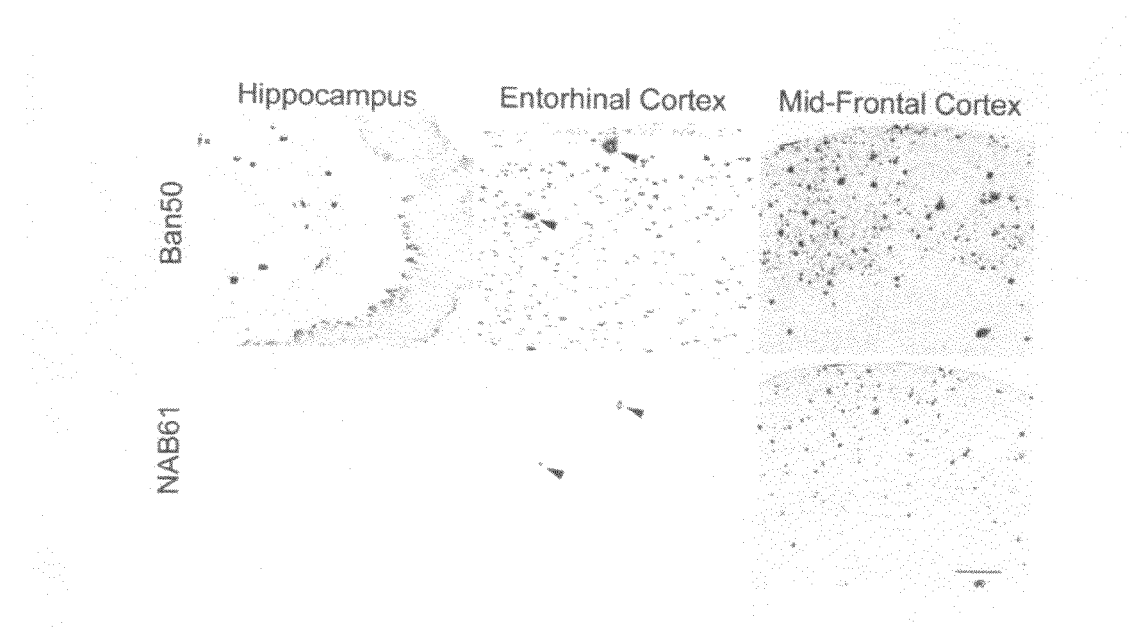
FIG. 4A
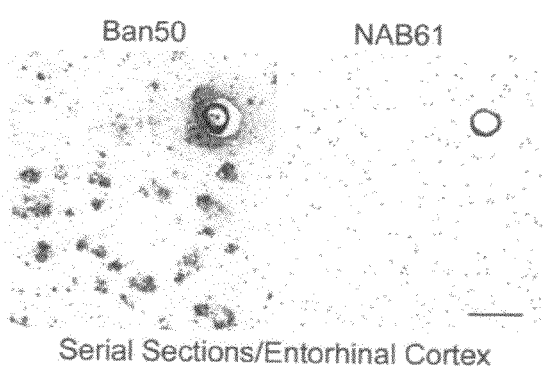
FIG. 4B
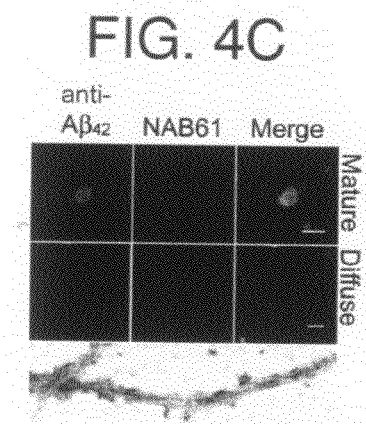
FIG. 4C
FIG. 4D

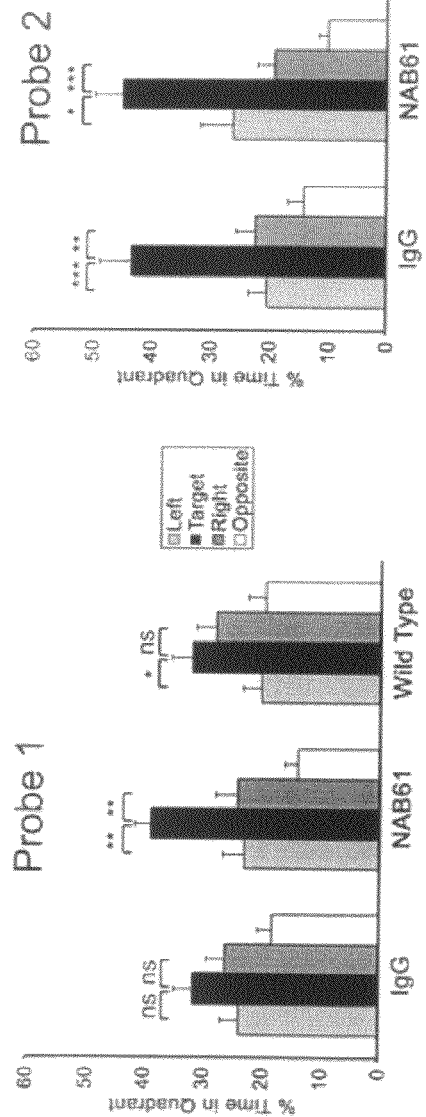
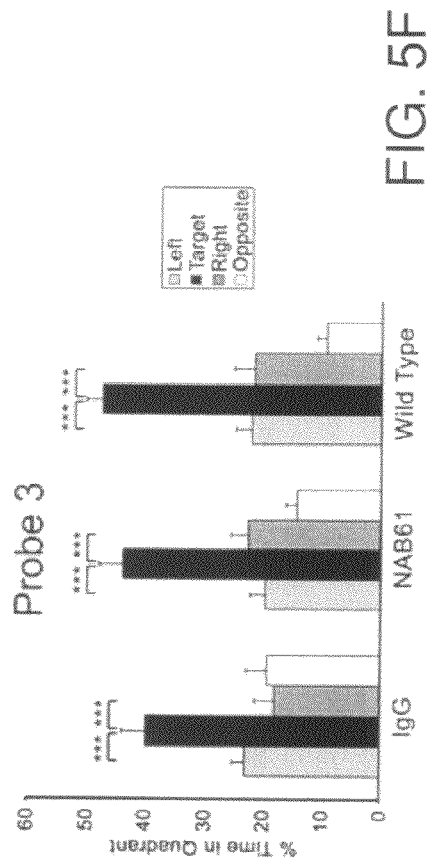
FIG. 5D
FIG. 5E
FIG. 5F

ANTIBODY TREATMENT OF ALZHEIMER'S AND RELATED DISEASES

GOVERNMENT SUPPORT

This invention was supported in part by funds obtained from the U.S. Government (National Institute on Aging Grant Number AG 11542), and the U.S. Government may therefore have certain rights in the invention.

FIELD OF THE INVENTION

The present invention relates generally to a method of treating β-amyloidogenic diseases. Specifically, a method of treating Alzheimer's disease and related diseases with an antibody is disclosed.

DEPOSIT STATEMENT

The hybridoma cell line NAB61 was deposited, in accordance with the Budapest Treaty, with the American Type Culture Collection (ATCC®) on May 1, 2015, under Accession Number PTA-122120. In accordance with 37 CFR §1.808, the depositors assure that all restrictions imposed on the availability to the public of the deposited materials will be irrevocably removed upon the granting of a patent.

BACKGROUND OF THE INVENTION

Alzheimer's disease (AD) is a progressive, neurodegenerative disorder and is the most common cause of dementia. The disease is characterized by two types of lesions in the brain, abnormal clumps of fibers, called amyloid plaques, and tangled bundles of fibers, called neurofibrillary tangles. Amyloid plaques (also called senile plaques) primarily comprise Aβ peptide. The Aβ peptide is released from the amyloid β protein precursor, APP, by the action of two secretases, and γ (reviewed in Haass, *EMBO J.* 23:483-488 (2004)). Depending on the γ secretase, Aβ is a 40 or 42 amino acid peptide. While APP is a membrane-spanning protein, Aβ is a soluble peptide. Aβ peptide, however, is highly hydrophobic and readily self-aggregates, forming oligomers. Aggregation of Aβ oligomers results in fiber formation, and the fibers eventually precipitate and develop into the amyloid plaques typical of Alzheimer's and other β amyloidogenic diseases.

Soluble oligomeric forms of Aβ have been postulated to contribute to the onset of AD, and it has been hypothesized that the Aβ peptide causes the pathologic and behavioral manifestations of Alzheimers's disease, including synaptic dysfunction and loss, neurofibrillary tangle formation, neuronal degeneration, and impaired memory (Lambert et al., *Proc. Natl. Acad. Sci. USA* 95:6448-6453 (1998); Hartley et al., *J. Neurosci.* 19:8876-8884 (1999); Walsh et al., *Science* 416:535-539 (2002)). Soluble Aβ levels are increased in individuals with mild cognitive dysfunction in the absence of overt Aβ pathology, and the levels of soluble Aβ levels appear to correlate better with neurofibrillary degeneration and the loss of synaptic markers than do amyloid plaques in AD patients (McLean et al., *Ann. Neurol.* 46:860-86 (1999); Lue et al., *Am. J. Pathol.* 155:853-862 (1999); Naslund et al., *JAMA* 283:1571-1577 (2000)). Similarly, decreases in synaptophysin immunoreactivity and impairments in synaptic transmission in APP transgenic mice precede the onset of microscopic Aβ amyloid pathology (Hsia et al., *Proc. Natl. Acad. Sci. USA* 96:3228-3233 (1999); Mucke et al., *J. Neurosci.* 20:4050-4058 (2000)).

A variety of methods designed to inhibit the production or enhance the clearance of Aβ are being developed as potential AD therapies. Indeed, immunization of murine models of Aβ amyloidosis inhibits senile plaque formation, and ameliorates associated cognitive impairments (Schenk, *Nature* 200:173-177 (1999); Bard et al., *Nat. Med.* 6:916-919 (2000); Janus et al., *Nature* 408:979-982 (2000); Morgan et al., *Nature* 408: 982-985 (2000); DeMattos et al., *Proc. Natl. Acad. Sci. USA* 98:8850-8855 (2001); Hartman et al., *Neurosci.* 25:6213-6220 (2005)).

Despite the development of meningoencephalitis in 6% of individuals immunized with the $A\beta_{42}$ peptide during a phase II clinical trial (Nicoll et al., *Nat. Med.* 9:448-452 (2003); Orgogozo et al., *Neurology* 61:46-54 (2003)), immunotherapy, especially passive immunization, remains a compelling potential treatment for AD. Interestingly, passive immunization of mouse models of AD-like Aβ plaques has been shown to rapidly reverse learning and memory deficits without affecting Aβ plaque pathology, indicating that neutralization of toxic Aβ species can quickly restore neuronal function in vivo (Dodart et al., *Nat. Neurosci.* 5:452-457 (2002); Kotilinek et al., *J. Neurosci.* 22:6331-6335 (2002)).

U.S. Pat. No. 6,913,745 discloses an antibody that selectively binds to an epitope of residues 1-5 of Aβ and its use in a passive immunization method for treating an Alzheimer's disease patient. Gong et al. (*PNAS* 100:10417-10422 (2003)) disclose polyclonal antibodies raised against oligomers of $A\beta_{1-42}$. The predominant oligomer detected by the polyclonal antibody is a tetramer. Lambert et al. (*J. Neurochem.* 79:595-605 (2001)) disclose polyclonal antibodies raised against oligomers of $A\beta_{1-42}$. The predominant oligomers detected by the polyclonal antibody are trimers and tetramers.

Prior to the present invention, there was an unmet need in the art for an antibody that selectively binds a conformation in toxic Aβ oligomers and does not cross-react with intact APP or C99 for use in passive immunization treatments of β-amyloidogenic diseases. The instant invention meets this need.

SUMMARY OF THE INVENTION

The invention is drawn to an antibody that binds selectively to a conformation-specific epitope formed by residues 1-11 of Aβ. As used herein, "selectively binds" refers to a significantly higher affinity for a particular epitope, as compared to other epitopes. The antibodies of the invention bind with a higher affinity to Aβ dimers or higher order Aβ oligomers, than to Aβ monomers. The difference in binding affinity between affinity for an oligomer, as compared to affinity for the monomer, is at least about 5-fold, more preferably 10-fold, and more preferably still 100-fold or more. Furthermore, the antibodies of the invention preferably do not cross-react with APP or C99, or with other amyloidogenic proteins, such as Lewy bodies. The invention is further drawn to a pharmaceutical composition comprising an antibody of the invention, as well as to methods of treating a β-amyloidogenic disease using the pharmaceutical composition.

In one embodiment, the invention is drawn to a passive immunization method of treating Alzheimer's disease in a subject using a pharmaceutical composition of the invention. Prophylactic treatment to prevent or delay the development of a β-amyloidogenic disease are also encompassed by the invention. Other uses for an antibody of the invention include diagnostic assays and in vitro and in vivo detection, such as in vivo imaging. Kits are also provided that are useful for such applications.

Additional objects, advantages and novel features of the invention will be set forth in part in the description, examples and figures which follow, and in part will become apparent to those skilled in the art on examination of the following, or may be learned by practice of the invention.

BRIEF DESCRIPTION OF THE DRAWINGS

FIG. 1A depicts images of immunoblots of Aβ oligomers by NAB61 and NAB228. Aβ is untreated, full length $A\beta_{1-40}$ (residues 1-40). Aβ-$NO_2$ is $A\beta_{1-40}$ treated with a peroxynitrite. UV-Aβ is $A\beta_{1-40}$ treated with UV light. HNE-Aβ is $A\beta_{1-40}$ treated with 4-hydroxynonenal. Aβ oligomers were electrophoresed and blotted with either NAB61 (left) or NAB228 (right).

FIG. 1B depicts images of immunoblots of Aβ oligomers immunoprecipitated by NAB61 (left) or NAB228 (right). Immunoprecipitates were electrophoresed and blotted with NAB228.

FIG. 4A is a series of images depicting the regional distribution of NAB61 immunoreactivity in the brains of individuals with Alzheimer's disease. Amyloid angiopathy and dense senile plaques are indicated by arrowheads.

FIG. 4B is a series of two images, at a higher magnification than those in FIG. 4A, of serial sections from the entorhinal cortex of an individual with AD.

FIG. 4C is a series of images depicting double-immunofluorescence-stained sections of the entorhinal cortex stained with polyclonal anti-$A\beta_{42}$ antibody (left column) and NAB61 (middle column). A merged image is shown in the right column.

FIG. 4D is an immunoelectron microscopy image of NAB61-stained synthetic $A\beta_{1-40}$ fibrils.

FIG. 5D depicts the results of the first probe test (day 7) measuring spatial reference memory, in terms of percent time in quadrant, for NAB61-treated Tg2576, IgG-treated Tg2576 and non-transgenic wild-type mice. (ns: not significant ($p>0.05$); * $p<0.05$, ** $p<0.01$)

FIG. 5E depicts the results of the second probe test (day 10) measuring spatial reference memory, in terms of percent time in quadrant, for NAB61-treated Tg2576, IgG-treated Tg2576 and non-transgenic wild-type mice. (* $p<0.05$),  $p<0.01$, * $p<0.001$)

FIG. 5F depicts the results of the third probe test (day 13) measuring spatial reference memory, in terms of percent time in quadrant, for NAB61-treated Tg2576, IgG-treated Tg2576 and non-transgenic wild-type mice. (*** $p<0.001$)

DETAILED DESCRIPTION OF CERTAIN PREFERRED EMBODIMENTS

Figure 1C:
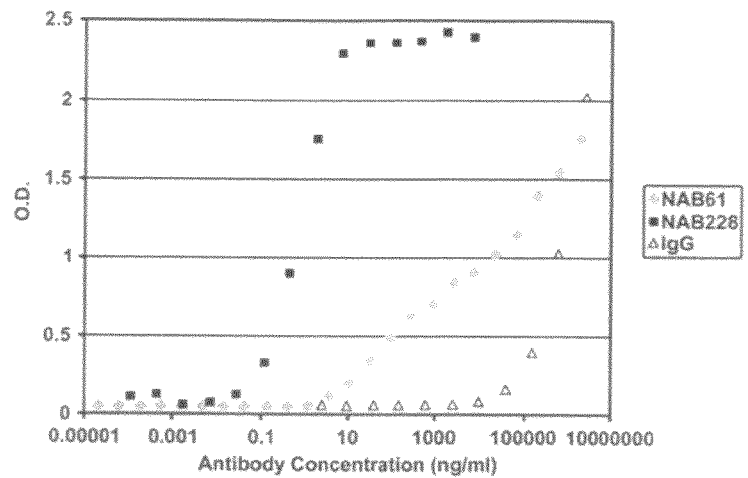
FIG. 1C is a graph showing solid-phase immunoreactivity of NAB61, NAB228 and non-specific mouse IgG on ELISA plates coated with $A\beta_{1-40}$.

The invention is drawn to an antibody that binds selectively to a conformation-specific epitope formed by residues 1-11 of Aβ. Specifically, the antibody binds selectively to an epitope formed by residues 1-11 of Aβ in an Aβ oligomer, including an Aβ dimer, trimer, tetramer, pentamer and higher order oligomers. The antibody further binds selectively to an epitope formed by residues 1-11 Aβ in an Aβ oligomer of a mature senile plaque, or binds selectively to an epitope formed by residues 1-11 Aβ in an Aβ oligomer of a pathologic Aβ deposit. The invention is exemplified by monoclonal antibody NAB61.

NAB61 specifically recognizes a pathologic Aβ conformation present early in the process of oligomerization which is maintained even in Aβ fibrils. It does not recognize other amyloidogenic proteins. It does not cross-react with APP or C99, indicating NAB61 may be a safer alternative for therapy compared with other monoclonal anti-Aβ antibodies. It is specific for Aβ, recognizing both oligomers, including dimers, trimers, tetramers and pentamers, and higher order Aβ structures. Passive immunization with NAB61 improved spatial learning and memory. Without being bound by theory, it is thought that NAB61 exerts its behavioral effect by blocking or neutralizing the biological activity of pathologic Aβ oligomers, without promoting the immune-mediated clearance of Aβ.

Diseases that may be treated by the methods of the invention are β-amyloidogenic diseases. β-amyloidogenic diseases are characterized by the presence of Aβ plaques or deposits. For instance, Alzheimer's disease is characterized by mature senile plaques comprising Aβ in extracellular regions of the brain. β-amyloidogenic diseases include, but are not limited to, Alzheimer's disease, Down's syndrome, mild cognitive impairment (MCI), cerebral amyloid angiopathy and hereditary cerebral hemorrhage with amyloidosis-Dutch type and -Icelandic type. In one embodiment of the invention, the β-amyloidogenic disease is Alzheimer's disease.

As used herein, the terms "treat" or "treatment" are used interchangeably and are meant to indicate delaying or even permanently delaying (i.e., preventing) development of a disease and/or a reduction in the severity of symptoms that will, or are expected to, develop. The terms further include ameliorating existing symptoms, preventing additional symptoms, and ameliorating or preventing the underlying metabolic causes of symptoms. Therefore, the methods of the invention encompass prophylactic applications to prevent or delay the onset of a β-amyloidogenic disease in a subject at risk for such a disease. For instance, subjects with a genetic predisposition to Alzheimer's are suitable candidates for prophylactic treatment according to the methods of the invention. The methods of the invention also encompass therapeutic treatments of a β-amyloidogenic disease in a subject diagnosed with such a disease. Prophylactic and therapeutic treatments also encompass removal of toxic Aβ oligomers ex vivo by plasmapheresis. Advantageously, passive immunization with an antibody of the invention may reverse cognitive dysfunction and improve memory, such as spatial memory, and learning in a subject with Alzheimer's disease.

Subjects suited for treatment using the methods of the invention are mammals, including humans. Other mammals include, but are not limited to, non-human primates, cattle, sheep, goats, rabbits, mice, etc, and include either domestic or wild-type species, or any other mammal subject to β-amyloidogenic disease.

The term "antibody," as used herein, refers to an immunoglobulin molecule which is able to specifically bind to a specific epitope on an antigen. As used herein, antibodies include intact immunoglobulins derived from natural sources or from recombinant sources, as well as immunoreactive portions of intact immunoglobulins. The immunoreactive portion of an intact immunoglobulin is also referred to herein as the "antigen binding portion." Antibodies are typically tetramers of immunoglobulin molecules. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), chimeric antibodies and humanized antibodies (Harlow et al., *Using Antibodies: A Laboratory Manual*, Cold Spring Harbor Laboratory Press, Cold Spring Harbor, N.Y. (1999); Harlow et al., *Antibodies: A Laboratory Manual*, Cold Spring Harbor Laboratory Press, Cold Spring Harbor, N.Y. (1989); Houston et al., *Proc. Natl. Acad. Sci. USA* 85:5879-5883 (1988); Bird et al., *Science* 242:423-426 (1988)). As used herein, a "neutralizing antibody" is an immunoglobulin molecule that binds to and blocks the biological activity of an antigen. In one embodiment, the antibody of the invention is a monoclonal antibody.

The antibodies of the invention further encompass synthetic antibodies. By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art. An intrabody is a particular type of synthetic antibody genetically engineered to be retained within a cell. An intrabody is encoded by a nucleic acid encoding the variable region of an antibody of the invention is fused to an intracellular retention sequence, such that, the resulting expression product is retained in a specific intracellular compartment. In the instant invention, such an intrabody may be used to bind selectively to an epitope formed by residues 1-11 Aβ in an Aβ oligomer prior to the secretion of Aβ, thereby inhibiting or preventing secretion. Intrabodies are well known in the art and are described in, for example, Marasco et al. (U.S. Pat. No. 6,004,940) and Beerli et al. (*Breast Cancer Research and Treatment* 38:11-17 (1996)).

As used herein, "humanized antibodies" refer to antibodies that have complementarity determining regions (CDR) from a non-human antibody, e.g., a mouse antibody, and variable region framework residues from a human antibody. If present, the constant region residues are from a human antibody. Such antibodies are advantageous when administered to a human because the possible immunogenicity of the antibody is reduced. Methods of making humanized antibodies are well known to the skilled artisan. See, for instance, Queen et al. (U.S. Pat. No. 6,180,370), Wright et al. (*Critical Rev. Immunol.* 12:125-168 (1992)) and Carter et al. (WO 92/22653). Humanized antibodies are preferred in the methods of the invention for treating β-amyloidogenic diseases when the subject is a human.

An antibody of the invention selectively binds to an epitope formed by residues 1-11 of Aβ in an Aβ oligomer. As used herein, "Aβ" refers to a peptide having the same or substantially the same amino acid sequence as the 40 amino acid sequence released from APP by proteolysis by β secretase and γ40 secretase. The terms "AB", "Aβ40" and "Aβ$_{1-40}$" are used interchangeably. Preferably, the antibody binds to an epitope formed by residues 1-11 of Aβ in an Aβ dimer. More preferably, the antibody binds to an epitope formed by residues 1-11 of Aβ in an Aβ dimer, Aβ trimer or an Aβ tetramer. More particularly, an antibody of the invention selectively binds to an epitope formed by residues 1-11 of Aβ in an Aβ oligomer of a mature senile plaque.

As used herein, a "mature senile plaque" refers to an extracellular amyloid structure found in the brains of Alzheimer's disease patients. A mature senile plaque is a typically roughly spherical structure with a dense Aβ amyloid core and is associated with neuritic alterations, tau pathologies or neuronal loss. Even more particularly, an antibody of the invention binds to an epitope formed by residues 1-11 Aβ in an Aβ oligomer of a pathologic Aβ deposit. As used herein, "pathologic Aβ deposit" refers to any microscopically abnormal accumulations of Aβ in the brain.

Antibodies of the invention may be made using any method known to the skilled artisan, using the appropriate antigen. The appropriate antigen is an Aβ oligomer. In one embodiment, an Aβ oligomer is generated, for instance, by crosslinking Aβ monomers, by chemical means, such as by exposure to peroxynitrite, or by exposure to ultraviolet (UV) light. Aβ monomers may be chemically synthesized, or be made by recombinant methods known to the skilled artisan. Aβ monomers may also be generated by enzymatic cleavage of, for instance, APP purified from an animal or from a recombinant cell expressing APP.

The generation of polyclonal antibodies is accomplished by inoculating the desired animal with the appropriate antigen, and then isolating antibodies which specifically bind the antigen therefrom.

Monoclonal antibodies directed against full length or active peptide fragments of a protein may be prepared using any well known monoclonal antibody preparation procedures, such as those described, for example, in Harlow et al., supra, 1989, and in Tuszynski et al., *Blood* 72:109-115 (1988)). Human monoclonal antibodies may be prepared by the method described in U.S. patent publication 2003/0224490. Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice or other mammals immunized with the peptide using standard procedures as referenced herein.

The nucleic acid sequence encoding the monoclonal antibody obtained using the procedures described herein may be cloned and sequenced using technology which is available in the art, and is described, for example, in Wright et al., supra, 1992 and the references cited therein. Further, the antibody of the invention may be "humanized" using the technology described in Wright et al., (supra (1992)) and in the references cited therein, and in Gu et al., *Thrombosis and Nematocyst* 77(4):755-759 (1997).

To generate a phage antibody library, a cDNA library is first obtained from mRNA which is isolated from cells, e.g., the hybridoma, which expresses the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., *Molecular Cloning: A Laboratory Manual*, Cold Spring Harbor Laboratory Press, Cold Spring Harbor, N.Y. (2001).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described, for example, by Wright et al., supra, 1992.

Processes such as those described above, have been developed for the production of human antibodies using M13 bacteriophage display (Burton et al., *Adv. Immunol.* 57:191-280 (1994)). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

Although the foregoing procedures describe the generation of phage which encode the Fab portion of an antibody molecule, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., (*J. Mol. Biol.* 222:581-597 (1991)). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, *Nature Medicine* 1:837-839 (1995); de Kruif et al., *J. Mol. Biol.* 248:97-105 (1995)).

Antibodies may be tested for epitope specificity by methods known in the art. Methods include assaying binding affinity for Aβ oligomers compared to binding affinity for Aβ monomers, for instance, by immunoblotting or immunoprecipitation. Other methods include a competition assay with an antibody whose epitope specificity has been already determined, such as NAB61.

An exemplary antibody of the invention is the monoclonal antibody, NAB61. Under the terms of the Budapest Treaty on the International Recognition of the Deposit of Microorganisms for the Purpose of Patent Procedure, deposit of the cell line producing the monoclonal antibody, NAB61, is being made with the American Type Culture Collection (ATCC) of Rockville, Md., USA.

Applicants' assignee, the Trustees of the University of Pennsylvania, represents that the ATCC is a depository afforded permanence of the deposit and ready accessibility thereto by the public if a patent is granted. All restrictions on the availability to the public of the material so deposited will be irrevocably removed upon granting of a patent. The material will be readily available during the pendency of the patent application to one determined by the Commissioner to be entitled thereto under 37 C.F.R. §1.14 and 35 U.S.C. §122. The deposited material will be maintained with all the care necessary to keep it viable and uncontaminated for a period of at least five years after the most recent request for the furnishing of a sample of the deposited material, and in any case, for a period of at least thirty (30) years after the date of the deposit or for the enforceable life of the patent, whichever period is longer. Applicants' assignee acknowledges its duty to replace the deposit should the depository be unable to furnish a sample when requested due to the condition of the deposit.

The therapeutic methods of the invention encompass the use of pharmaceutical compositions of an antibody that selectively binds to an epitope formed by residues 1-11 of Aβ in an Aβ oligomer, an antibody that selective binds to an epitope formed by residues 1-11 of Aβ in an Aβ dimer, an antibody that selective binds to an epitope formed by residues 1-11 of Aβ in an Aβ dimer, an Aβ trimer and an Aβ tetramer, an antibody that selectively binds to an epitope formed by residues 1-11 of Aβ in an Aβ oligomer of a mature senile plaque protein or an antibody that selective binds to an epitope formed by residues 1-11 of Aβ in an Aβ oligomer of a pathologic Aβ deposit to practice the methods of the invention. The pharmaceutical compositions further comprise a pharmaceutically-acceptable carrier.

As used herein, the term "pharmaceutically-acceptable carrier" means a chemical composition with which an antibody that selectively binds to an epitope formed by residues 1-11 of Aβ in an Aβ oligomer, an antibody that selective binds to an epitope formed by residues 1-11 of Aβ in an Aβ dimer, an antibody that selective binds to an epitope formed by residues 1-11 of Aβ in an Aβ dimer, an Aβ trimer and an Aβ tetramer, an antibody that selectively binds to an epitope formed by residues 1-11 Aβ in an Aβ oligomer of a mature senile plaque protein or an antibody that selective binds to an epitope formed by residues 1-11 Aβ in an Aβ oligomer of a pathologic Aβ deposit may be combined and which, following the combination, can be used to administer the antibody to a mammal.

The formulations of the pharmaceutical compositions described herein encompass those prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially-relevant mammals, such as non-human primates, cattle, pigs, horses, sheep, goats, cats, and dogs, etc, as further defined above.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal, or another route of administration. Other contemplated formulations include projected nanoparticles, liposomal preparations, and resealed erythrocytes containing the active ingredient.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents or adjuvants. Controlled- or sustained-release formulations of a pharmaceutical composition of the invention may be made using conventional technologies.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraventricular (into the brain's ventricles), subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile, injectable, aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils, such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example, in *Remington's Pharmaceutical Sciences* (1985, Genaro, ed., Mack Publishing Co., Easton, Pa.), which is incorporated herein by reference.

Typically dosages of the antibody of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. Preferably, the dosage of the antibody will vary from about 1 mg to about 10 g per kilogram of body weight of the animal. More preferably, the dosage will vary from about 10 mg to about 1 g per kilogram of body weight of the animal.

The pharmaceutical composition of the invention may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. In addition, the blood level of the antibody administered in the pharmaceutical composition may be monitored in the subject as another factor in determining the dose frequency.

The antibodies of the invention are also useful in methods of diagnosis or other immunological detection assays. For diagnosis of a β-amyloidogenic disease, such as Alzheimer's disease, an antibody of the invention may be used in an ELISA or other immunoassay to detect the presence of Aβ oligomers, including dimers, trimers, tetramer and pentamers, mature senile plaques and/or pathologic Aβ deposits in a biological sample. Biological samples suitable for diagnostic applications include, but are not limited to, brain tissue, blood, plasma, cerebrospinal fluid (CSF), saliva, tears, nasal discharges, urine, feces and any other biological sample that can be assayed for Aβ.

Antibodies of the invention may also be used for in vivo imaging procedures to detect Aβ oligomers, including dimers, trimers, tetramer and pentamers, mature senile plaques and/or pathologic Aβ deposits. In vivo imaging is useful for diagnostic purposes, such as the diagnosis of Alzheimer's disease. It may also be performed prior to symptoms of disease to assess risk of development. For use with in vivo imaging, an antibody of the invention is appropriately labeled for detection by PET, optical detection, single photon emission computed tomography, or other detection means. The labeled antibody is administered to the subject, for instance, intravenously, intranasally or intraventricularly. The antibody may also be attached, covalently or noncovalently, to a molecule to increase passage across the blood-brain barrier, for instance, a polyamine moiety.

Immunological assays useful in the present invention include various immunoassays, for example, immunohistochemistry assays, immunocytochemistry assays, ELISA, capture ELISA, sandwich assays, enzyme immunoassay, radioimmunoassay, fluorescent immunoassay, agglutination assays and the like, all of which are known to those of skill in the art. See, e.g., Harlow et al., supra, 1989 and 1999.

Enzyme linked immunoadsorbent assays (ELISA) are useful in the methods of the present invention. In an ELISA assay, proteins or peptides are immobilized onto a selected surface, preferably a surface exhibiting a protein affinity, such as the wells of a polystyrene microtiter plate. After washing to remove incompletely adsorbed material, it is desirable to bind or coat the assay plate wells with a nonspecific protein that is known to be antigenically neutral with regard to the test antisera, such as bovine serum albumin (BSA), casein or solutions of milk powder. This allows for blocking of non-specific adsorption sites on the immobilizing surface, and thus reduces the background caused by nonspecific binding of antisera onto the surface.

After binding of antigenic material to the well, coating with a non-reactive material to reduce background, and washing to remove unbound material, the immobilizing surface is contacted with the antisera, or with a clinical or biological sample to be tested in a manner conducive to immune complex (antigen/antibody) formation. Such conditions preferably include diluting the antisera with diluents such as BSA, bovine gamma globulin (BGG), phosphate buffered saline (PBS)/Tween, and the like. These added agents also tend to assist in the reduction of nonspecific background. The layered antisera is then allowed to incubate for greater than about one hour, at temperatures preferably on the order of about 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing; the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a biotin or peroxidase-conjugated anti-appropriate-animal IgG for a period of time and under conditions which favor the development of immunocomplex formation (e.g., incubation for about 2 hours at room temperature in a PBS-containing solution, such as PBS/Tween).

After incubation with the second tagged antibody, and subsequent to washing to remove unbound material, the amount of label is quantified by incubation with a chromogenic substrate, such as urea and bromocresol purple, or 2,2'-azino-di-(3-ethyl-benzthiazoline-6-sulfonic acid) ("ABTS") and hydrogen peroxide ($H_2O_2$), in the case of peroxidase as the enzyme label. Quantification is then achieved by measuring the degree of color generation, e.g., using a visible spectra spectrophotometer.

The invention further provides kits useful in the practice of the methods of the invention, for instance, to diagnose Alzheimer's disease or to detect Aβ oligomers, including dimers, trimers, tetramer and pentamers, in a biological sample. The kits comprise a container comprising an antibody of the invention and an instructional material for the use thereof. As used herein, an "instructional material" includes a publication, a recording, a diagram, or any other medium of expression which can be used to communicate the usefulness of the kit in detecting, for instance, Aβ oligomers, including dimers, trimers, tetramer and pentamers, mature senile plaques and/or pathologic Aβ deposits. The instructional material of the kit of the invention may, for example, be affixed to a container containing the antibody, or be shipped together with a container containing the medium. Alternatively, the instructional material may be shipped separately from the container with the intention that the instructional material and the antibody be used cooperatively by the recipient. The kits can also contain any other component useful in the practice of the inventive methods including, but not limited to, a container for a biological sample, other Aβ antibodies, for instance ones that detect Aβ monomers, and positive and negative control samples.

The present invention is further described in the following examples. These examples are provided for purposes of illustration only, and are not intended to be limiting unless otherwise specified. The various scenarios are relevant for many practical situations, and are intended to be merely exemplary to those skilled in the art, but are not to be construed as limiting the scope of the appended claims. Thus, the following examples should be construed to encompass any and all variations which become evident in light of the teaching provided herein.

EXAMPLES

The materials and methods used in the Examples below are now described.

Generation of NAB61:

Synthetic $Aβ_{1-40}$ (W. M. Keck Facility, Yale University) was treated either with peroxynitrite (as described in Norris et al., *J. Biol. Chem.* 278:27230-27240 (2003)), UV-light or by 4-hydroxynonenal. Balb-c mice were immunized with 100 μg of Aβ emulsified with complete Freund's adjuvant, followed by three additional injections of 25 g of Aβ emulsified with incomplete Freund's adjuvant every third week. Isolated lymphocytes were used to generate hybridomas by fusion with Sp2/O—Ag14 myeloma cells with polyethylene glycol 1500.

Immunoprecipitation and Immunoblotting:

Synthetic Aβ preparations (0.5 μg) were electrophoresed on a 16% Tris-tricine gel and immunoblotted with NAB228 or NAB61. Aβ was also subject to immunoprecipitation by NAB228 or NAB61 with protein A/G agarose beads (Santa Cruz Biotechnology) followed by electrophoresis on a 16% Tris-tricine gel and immunoblotting with NAB228. For immunoprecipitation of APP and C-terminal APP fragments, 10 cm dishes of CHO Pro5 cells were transfected with 10 μg of pcDNA3.1 containing the cDNA for either green fluorescent protein or APPswe. Cells were radiolabeled with [$^{35}$S]-methionine for 2 hours in the presence of 200 μM MG 132 to enhance the accumulation of C-terminal APP fragments. Cell lysates were collected in RIPA buffer (0.5% sodium deoxycholate, 0.1% SDS, 1% Nonidet P-40, 5 mM EDTA in TBS, pH 8.0) containing protease inhibitors (1 μg/ml of pepstatin A, leupeptin, L-1-tosylamido-2-phenylethyl chloromethyl ketone, 1-chloro-3-tosylamido-7-amino-2-heptanone, and soybean trypsin inhibitor, and 0.5 mM phenylmethylsulfonyl fluoride) followed by centrifugation at 100,000×g for 20 min at 4° C. RIPA lysates were subject to immunprecipitation with a panel of monoclonal antibodies that recognize $Aβ_{1-11}$ (NAB14, NAB61, NAB89, NAB229, Ban50), a rabbit polyclonal antibody raised against the C-terminus of APP (2493) and a goat polyclonal antibody raised against the N-terminal ectodomain of APP (Karen). Immunoprecipitates were electrophoresed on a 10/16.5% step gradient Tris-tricine gel, fixed with methanol, dried and exposed to a phosphorimager screen for visualization.

To detect APP and APP fragments from mouse brain extracts, cortical RIPA lysates were immunoprecipitated with a rabbit polyclonal antibody raised against the C-terminus (5685) and electrophoresed on either a 7.5% Tris-glycine gel for APP or a 10/16.5% Tris-tricine gel for C-terminal APP fragments. Full length APP was immunoblotted with Karen while C-terminal APP fragments were immunoblotted with 5685. sAPPβswe derived from APPswe was immunoblotted with 54, a rabbit polyclonal antibody specific for sAPPβswe.

To detect peripheral Aβ, 200 μl of plasma was diluted with RIPA buffer and immunoprecipitated with 4G8 (anti-$Aβ_{17-24}$) which was covalently conjugated to protein A/G beads with dimethyl pimelimidate to prevent competition with endogenous IgG. Immunoprecipitates were electrophoresed on a 10/16.1% Tris-tricine gel and immunoblotted with 4G8.

Immunocytochemistry and Immuno-Electron Microscopy:

Neuro2A, CHO Pro5 and NT2N neurons were transduced with a Simliki Forest Virus encoding APPswe (SFV-APPswe) (Formant et al., *J. Biol. Chem.* 272:32247-3225 (1997) and Liljestrom et al., *Bio/Technology* 9:1356-1361 (1991)). After 16 hours, cells were fixed with cold 95% ethanol/5% acetic acid for 10 minutes followed by further permeabilization with 0.2% Triton-X 100 in PBS for 10 minutes. Cells were stained with a goat polyclonal N-terminal APP antibody (Karen) and with NAB61, followed by FITC-conjugated anti-goat IgG and Texas Red-conjugated anti-mouse IgG. For immuno-electron microscopy, CHO Pro5 and NT2N neurons were plated in Millicell-CM culture plate inserts, transduced with SFV-APPswe, and fixed with 4% paraformaldehyde/0.5% glutaraldehyde. Fibrillar synthetic $Aβ_{40}$ was absorbed to 300 mesh carbon coated copper grids, washed with PBS and blocked with 1% bovine serum albumin in PBS. Fibrils were stained with NAB61 followed by anti-mouse IgG conjugated to 5 nm colloidal gold particles. After washing with PBS, grids were stained with 1% uranyl acetate, dried and visualized with a Joel 1010 transmission electron microscope (Joel USA, Peabody, Mass.).

Immunohistochemistry:

Tissue blocks from human subjects were removed at autopsy and immersion fixed in 70% ethanol with 150 mM NaCl, or 10% buffered formalin. For murine tissue, deeply anesthetized mice were transcardially perfused with heparinized PBS and brains were surgically removed and immersion fixed in 10% neutral buffered formalin for 24 hrs. Samples were dehydrated through a series of graded ethanol solutions to xylene, and infiltrated with paraffin as described (Trojanowski et al., *J. Histochem. Cytochem.* 37:209-215 (1989)). Sections (6 μm) were stained using standard avidin-biotin-peroxidase methods using 3-3' diamino-benzedene. Ban50 (mouse anti-A$\beta_{1-10}$), NAB228 (mouse anti-A$\beta_{1-11}$), 4G8 (mouse anti-A$\beta_{17-24}$) and NAB61 (mouse anti-oligomer-A$\beta_{1-11}$) were used as primary antibodies. For immunofluorescence, sections were stained with a rabbit polyclonal anti-A$\beta_{42}$ antibody (QCB) and with NAB61 followed by FITC-conjugated anti-rabbit IgG and Texas Red-conjugated anti-mouse IgG. Thioflavin S staining of formalin-fixed tissue was used to detect fibrillar A$\beta$ deposits.

ELISA Analysis:

For solid-phase ELISA analysis, ELISA plates were coated with A$\beta$ at 1 μg/ml in PBS at 4° C. overnight. Plates were blocked with 5% fetal bovine serum in PBS and antibodies diluted in 5% FBS/PBS were incubated at 4° C. overnight, and bound antibodies were detected with HRP conjugated anti-mouse IgG (Jackson Immunoresearch, West Grove, Pa.). For blocking experiments, ELISA plates were coated with A$\beta_{1-40}$ at 0.1 μg/ml in PBS, and antibodies were preincubated with the indicated blocking peptides 10 μg/ml. For capturing experiments, ELISA plates were coated with either NAB61 or Ban50 at 10 μg/ml in PBS and blocked with 1% casein in PBS. A$\beta$ peptides diluted in blocking buffer 10 μg/ml were incubated at 4° C. overnight, and bound A$\beta$ was detected with HRP conjugated BA27 (mouse anti-A$\beta_{40}$).

Cortical and hippocampal regions were dissected, and stored at −80° C. until the samples were processed. Detergent-soluble fractions were obtained by sonicating samples in 1 ml of RIPA buffer containing protease inhibitors for every 150 mg of tissue. After centrifugation at 100,000×g for 20 min at 4° C., the resulting pellet was solubilized by sonication in 70% FA followed by another round of centrifugation. Detergent-soluble and insoluble supernatants were assayed by sandwich ELISA as previously described (Lee et al., *J. Biol. Chem.* 278:4458-4466 (2003)). Briefly, ELISA plates were coated with either JRF/c40 or JRF/c42 to capture A$\beta_{40}$ and A$\beta_{42}$, respectively. After application of diluted samples and a standard curve consisting of serially-diluted synthetic A$\beta$ (Bachem Biosciences, King of Prussia, Pa.), the concentration of A$\beta$ was determined by using horseradish-peroxidase-conjugated m266 (anti-A$\beta_{13-28}$) as a reporting antibody. These antibodies do not recognize the N-terminus of A and therefore do not compete with NAB61 for A$\beta$.

Immunization and Behavioral Analysis:

Tg2576 mice, transgenic mice that overexpress human APP harboring the Swedish mutation (APPswe; Hsiao et al., *Science* 274:99-102 (1996)), were maintained on a C57B6/SJL F2 background by successive backcrossing to wild-type C57B6/SJL F1 females. All mice were generated and handled according to University of Pennsylvania Institutional Animal Care and Use Committee guidelines.

Short Term Passive Immunization:

17-19 month old Tg2576 littermates and wild-type littermates were administered an initial dose of 400 μg NAB61 or non-specific mouse IgG intraperitoneally (day −3) followed by maintenance doses of 200 μg after 3, 9 and 15 days (days 0, 6 and 12). To test spatial learning and memory behavior, mice were tested in both the visible platform version (on days 1 through 3) and the hidden platform version (on days 4 through 13) of the Morris Water Maze (MWM). The protocol was performed as described by Westerman et al. (*J. Neurosci.* 22:1858-1867 (2002)) in which non-performing mice with known sensorimotor and behavioral abnormalities were excluded by a blinded observer. Exclusion criteria included retinal degeneration in mice homozygous for a mutation in rd, visual defects due to albinism, and abnormal swimming behaviors (corkscrew circling, thigmotaxis and floating) that preclude the assessment of learning.

Mice were pre-handled for 3 days prior to testing in the MWM. The water maze was a circular pool (120 cm in diameter) filled with 20-25° C. water made opaque with tempera nontoxic paint. Fixed visual cues surrounded the water maze for spatial reference. Mice were gently lowered so that they were facing the wall of the pool. During the visual platform trials, the location of a circular platform (11.2 cm in diameter) was varied (NE, SE, SW, NW), as was the start position of the mouse (N, S, W, E). Mice received 2 blocks/day consisting of 4 trials/block. The platform was marked with a visual cue for easy identification.

For the hidden platform version of the MWM, the platform was hidden 0.5 cm below the water at a constant location throughout the training while the start position of the mouse was varied. Mice received 4 trials/day in which they searched for the platform for a maximum of 60 seconds. After finding the platform, mice were allowed to remain for 30 seconds. Each trial was separated by 4-6 minutes. The path of the mouse was recorded using a video tracking system (HVH Image, San Diego, Calif.) and latency to finding the platform was noted.

Interspersed between hidden platform trials were probe trials (days 7, 10 and 13) in which swimming paths in the absence of a platform were recorded for 60 sec, after which the platform is returned to the pool and the mouse was allowed to stay on the platform for 30 seconds. The probe trials were to measure the acquisition and retention of spatial reference memory throughout training. All mice were tested in a blinded manner, with groups balanced for genotype and treatment. Parameters, such as start position and platform placement, were pseudo-randomized so that all variations were tested. Mice were sacrificed three days after the termination of the MWM for biochemical and histological assessment.

Long-Term Passive Immunization:

Long-term passive immunization was performed on a cohort of 8 month-old Tg2576 mice, to which NAB61 or specific IgG were administered for 6 months, and sacrificed at 14 months of age. Tg2576 mice were treated with weekly intraperitoneal injections of 500 μg of non-specific IgG (n=8) or NAB61 (n=9) from 8 to 14 months. Changes in A$\beta$ deposits by immunohistochemistry and A$\beta$ levels by ELISA were conducted as described above. Detergent-soluble and insoluble fractions were obtained from the cortex and hippocampus of treated mice by sequential extraction with RIPA buffer and formic acid.

APP Processing in NAB61 Immunized Mice:

Full-length APP was immuno-precipitated with a C-terminal APP antibody (5685) and immunoblotted with an N-terminal APP antibody (Karen). sAPPβswe levels were assessed by immunoblotting with an end-specific polyclonal antibody (antibody 54). C99 was immunoprecipitated with NAB228, run on a 10/16.5% Tris-tricine gel and immunoblotted with 5685. β-tubulin was immunoblotted with TUB2.1.

Aβ Amyloid Pathology in NAB61 Immunized Mice:

Serial sections from the brains of Tg2576 mice treated with either non-specific IgG or NAB61 were subjected to immunohistochemistry using either NAB228 or NAB61 as primary antibodies.

Quantification of Aβ Accumulation in NAB61 Immunized Mice:

Cortical and hippocampal regions were subjected to sequential extraction, first with RIPA, followed by 70% formic acid (FA). Aβ concentrations were measured by sandwich ELISA specific for Aβ40 and Aβ42.

Peripheral Pools of Aβ in NAB61 Immunized Mice:

Plasma samples from Tg2576 mice treated with either non-specific IgG or NAB61 were subject to immunoprecipitation and immunoblotting with 4G8.

Intracerebral NAB61 Injection in APP×PS1 Transgenic Mice:

Tg2576 mice were mated with mice expressing presenilin harboring an FAD mutation to generate bigenic APP/PS mice as described (Lee et al., *FEBS Lett.* 579:2564-2568 (2005); Siman et al., *J. Neurosci.* 20(23):8717-26 (2000); Flood et al., *Neurobiol. Aging.* 23(3):335-48 (20021)). Intrahippocampal injections were performed with a 33-gauge needle (Hamilton Co, Reno, Nev.) using a stereotaxic apparatus (David Kopf Instruments, Tujunga, Calif.) at the following coordinates relative to bregma: −2.3 mm posterior, +2.0 mm lateral, and −1.8 mm ventral. Mice received 2 µl of NAB61 or non-specific IgG (Sigma, St. Louis, Mo.) at 2 µg/µl. Aβ amyloid burden ipsilateral and contralateral to the injection site was determined as described (Lee et al., supra (2005)), and the ratio of ipsilateral to contralateral Aβ amyloid burden was calculated.

Example 1

Generation of an Oligomer-Selective Monoclonal Antibody

The role of Aβ oligomers is difficult to assess in vivo due to the dearth of conformation-specific molecular tools. Towards this end, a monoclonal antibody that selectively recognizes oligomeric Aβ was generated by using a stable oligomeric Aβ preparation as antigen. Peroxynitrite is a reactive species generated by the reaction between superoxide and nitric oxide. Treating synthetic $A\beta_{1-40}$ with peroxynitrite resulted in the formation of SDS-stable Aβ oligomers, as shown by SDS-PAGE followed by immunoblotting with NAB228, a monoclonal antibody that recognizes a linear N-terminal Aβ epitope (FIG. 1A, right panel). Additional stable Aβ oligomers were generated by treating $A\beta_{1-40}$ with UV light or with the lipid-derived reactive aldehyde, 4-hydroxynonenal (from D. Teplow and T. Montine). Over 5,500 hybridoma supernatants were tested for the presence of Aβ antibodies. One hybridoma, NAB61, was isolated that produced an $IgG_1$ with selectivity towards oligomeric Aβ species. As demonstrated by both immunoblotting and immunoprecipitation, NAB61 showed selectivity towards SDS-stable Aβ oligomers, including dimers, trimers, tetramers, pentamers and higher order oligomers, relative to monomeric Aβ (FIGS. 1A and B, left panels), in notable contrast with other Aβ antibodies, such as NAB228 (FIGS. 1A and B, right panels).

Figure 1D:
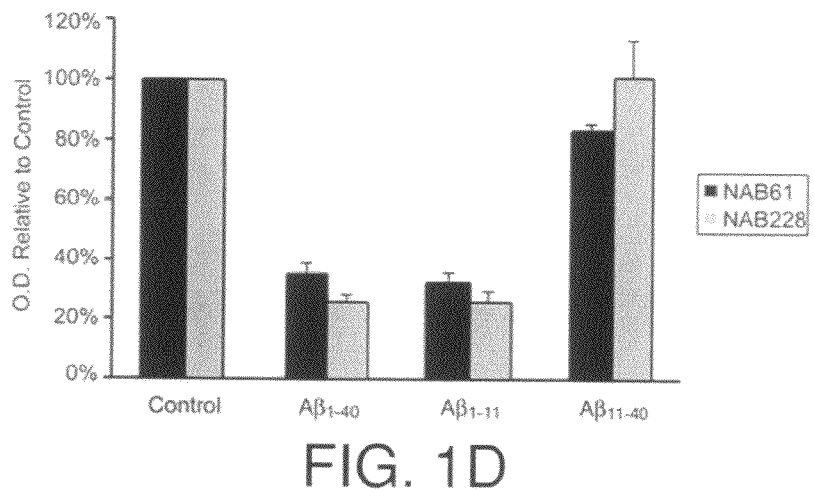
FIG. 1D is a bar graph depicting the results of solid-phase ELISA immunoreactivity assays of NAB61 and NAB228 preincubated with peptides corresponding to full length $A\beta_{1-40}$, $A\beta_{1-11}$ (N terminal residues 1-11), or $A\beta_{11-40}$ (C terminal residues 11-40).
Figure 1E:
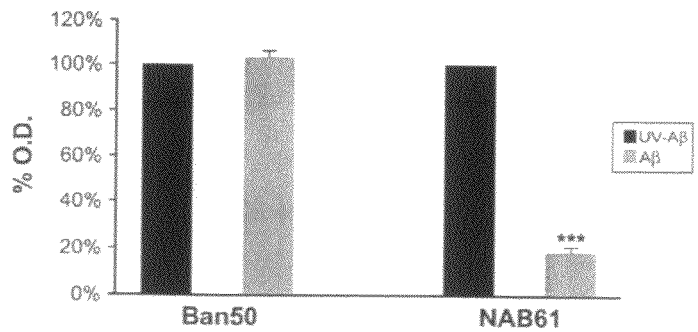
FIG. 1E is a bar graph depicting the results of a sandwich ELISA using Ban50 or NAB61 as the capturing antibody for Aβ or UV-cross linked Aβ(UV-Aβ). Captured peptides were detected with HRP-conjugated BA27 (anti-$A\beta_{40}$). A two-tailed t-test was performed on O.D. readings performed in duplicate from two independent experiments (*** $p<0.001$).

To further characterize this novel monoclonal antibody, NAB61 was examined in a variety of additional immunologic assays. When tested in a solid-phase ELISA format in which $A\beta_{1-40}$ was coated onto plastic, NAB61 titers were very low relative to NAB228 (FIG. 1C). Despite this low immunoreactivity, peptides corresponding to $A\beta_{1-11}$ and $A\beta_{1-40}$ blocked the signal generated by NAB61, while $A\beta_{11-40}$ did not (FIG. 1D). This observation indicated that NAB61 recognizes an N-terminal Aβ epitope. When used as a capturing antibody in a sandwich ELISA format, NAB61 had greater affinity for oligomeric Aβ relative to non-oligomeric Aβ in contrast with other anti-Aβ monoclonal antibodies, such as Ban50 (FIG. 1E). These in vitro studies indicate that NAB61 recognizes a complex conformational epitope found in the N-terminus of oligomeric forms of Aβ.

Figure 2A:
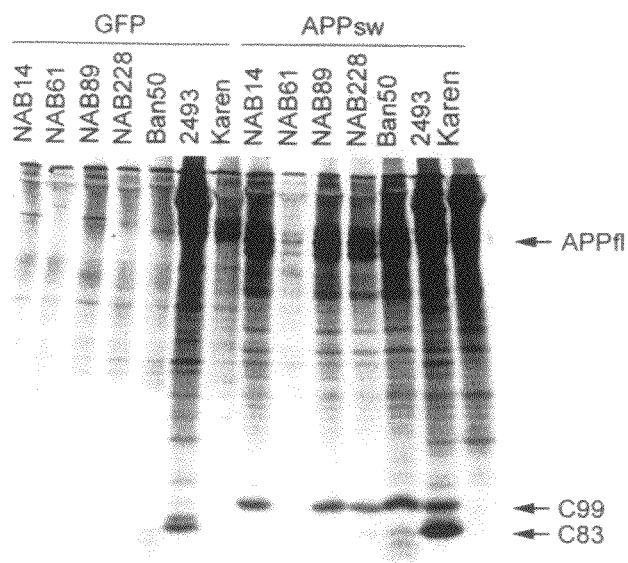
FIG. 2A is an image of immunoprecipitated material from CHO Pro5 cells transfected with either GFP (left) or APPswe (right) and radiolabeled with [$^{35}$S]-methionine. RIPA lysates were immunoprecipitated with one of a panel of N-terminal murine monoclonal antibodies (NAB14, NAB61, NAB89, NAB228 and Ban50), a rabbit polyclonal antisera (2493) raised against the C-terminus of APP, or a goat polyclonal antisera (Karen) raised against the N-terminal ectodomain of APP (sAPP). "APPswe" refers to APP holoprotein bearing the Swedish AD mutation.
Figure 2B:
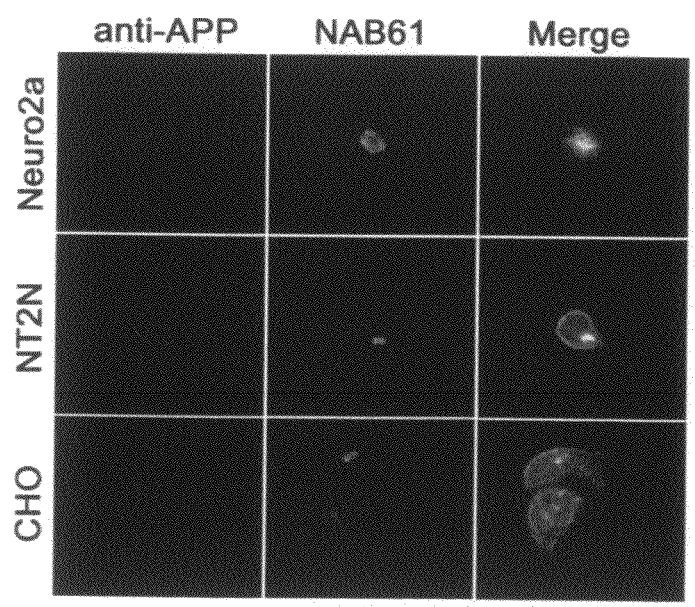
FIG. 2B is a series of images of double-immunofluorescence stained Neuro2A (top row), NT2N neurons (middle row) and CHO Pro5 cells (bottom row) transduced with an SFV-APPswe vector (a Simliki Forest Virus encoding APPswe). Anti-APP (left column) is N-terminal APP polyclonal antibody Karen. NAB61 is in the middle column. A merged image is shown in the right column with a DAPI counterstain for nuclei.

Although the primary sequence of Aβ is present in full length APP and C-terminal APP fragments, such as C99, an antibody which recognizes a pathologic Aβ conformation should be specific for the Aβ peptide. Therefore, it was hypothesized that NAB61 would not recognize full length APP or C99. Immunoprecipitations from radiolabeled CHO cells overexpressing either GFP or APP were performed with a panel of monoclonal antibodies that recognize the N-terminus of Aβ (designated NAB antibodies), a polyclonal N-terminal APP antibody, and a polyclonal C-terminal APP antibody. All of the NAB antibodies recognized both full length APP and C99, with the notable exception of NAB61 (FIG. 2A). The lack of cross-reactivity with APP was confirmed by double immunofluorescence staining of Neuro2a, NT2N and CHO cells overexpressing APPswe (FIG. 2B). This experiment showed that NAB61 staining did not co-localize with staining of total APP by a polyclonal N-terminal APP antibody. Therefore, NAB61 recognizes a conformational epitope specific to oligomeric Aβ that is not present in the Aβ sequence in the structural context of APP or C99.

Example 2

NAB61 Immunoreactivity Against Fibrillar Aβ Amyloid

Figure 3:
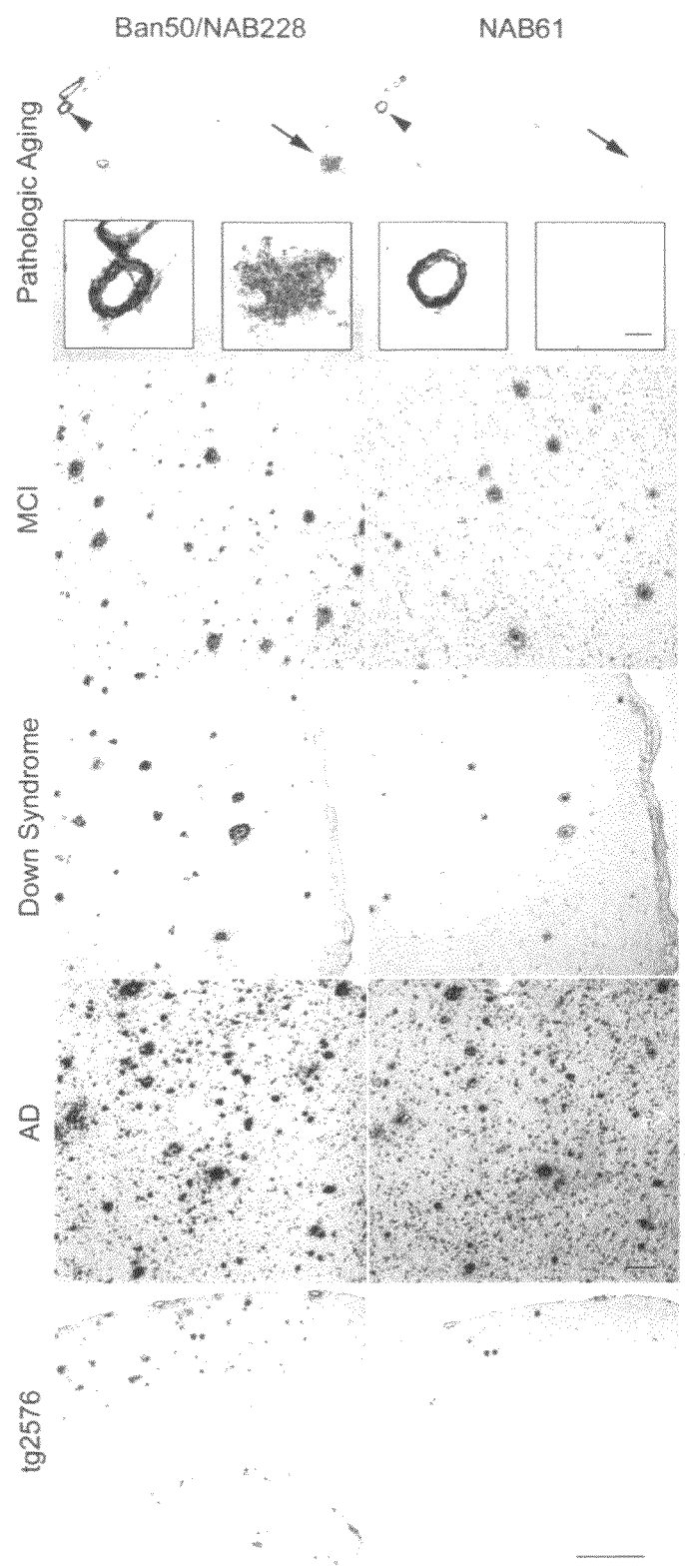
FIG. 3 is a series of images of sections from a variety of pathologic specimens stained with either Ban50/NAB228 (left) or NAB61 (right), and counterstained with hematoxylin for nuclei. Insets show a higher magnification view of a blood vessel with amyloid angiopathy (left) or a diffuse Aβ deposit (right) from the mid-frontal cortex. All images were taken from serial sections with the exception of the individual with MCI. MCI=mild cognitive impairment. DS=Down's syndrome. AD=Alzheimer's disease. Tg2576=transgenic mice overexpressing human APP with Swedish mutation.

To ensure that NAB61 recognizes bona fide Aβ amyloid, immunohistochemistry was performed on a variety of tissues containing Aβ amyloid plaques. Individuals with pathologic aging (no history of cognitive impairment despite the presence of Aβ amyloid deposits), mild cognitive impairment (MCI) as demonstrated by psychometric testing, Down's syndrome (DS) and AD all contained Aβ plaques and other Aβ deposits that were NAB61 immunoreactive (FIG. 3). Interestingly, diffuse amyloid plaques were poorly stained by NAB61, despite robust staining of amyloid angiopathy (see FIG. 3 insets for pathologic aging). Compact amyloid plaques from Tg2576 transgenic mice overexpressing APPswe were also recognized by NAB61 (FIG. 3).

The initial stages of AD pathology are generally characterized by Aβ amyloid pathology in association cortices, such as the mid-frontal cortex. With disease progression, Aβ amyloid in neocortical regions becomes more advanced, co-incident with the development of relatively milder Aβ deposits in limbic regions, such as the entorhinal cortex and the hippocampus (Braak et al., *Acta Neuropathol* (Berl) 82:239-259 (1991)). NAB61 immunoreactivity generally exhibited regional selectivity, which reflected the regional progression and severity of Aβ amyloid pathology. For example, many diffuse amyloid deposits in the hippocampus and entorhinal cortex of Aβ brains were poorly stained by NAB61 (FIG. 4A, left and middle panels) despite strong staining of mature senile plaques and amyloid angiopathy (FIG. 4A, arrowheads, and FIG. 4B). Aβ amyloid plaques in the mid-frontal cortex, where dense, mature senile plaques predominate in AD, showed more robust NAB61 immunoreactivity (FIG. 4A, right panels).

The regional selectivity of NAB61 immunoreactivity confirmed that NAB61 recognizes a conformation that is found in advanced, pathologic Aβ deposits, namely mature senile plaques and amyloid angiopathy. These inclusions are distinct from diffuse Aβ deposits, which are not associated with neuritic alterations, tau pathologies or neuronal loss. Double immunofluorescence staining demonstrated that many amorphous Aβ deposits, which were recognized by a conventional polyclonal anti-Aβ42 antibody, were not recognized by NAB61 (FIG. 4C). In contrast, mature, dense, cored senile plaques were labeled by both antibodies (FIG. 4C). Given that Aβ fibrils are the ultrastructural building blocks of senile plaques, NAB61 staining of synthetic Aβ fibrils as viewed by immunoelectron microscopy, further corroborated the ability of NAB61 to recognize pathologic forms of Aβ (FIG. 4D). Therefore, NAB61 recognizes a pathologic conformation present in dimeric and higher order oligomeric Aβ which is maintained during fibrillization and coalescence into senile plaques. By comparison, NAB61 did not recognize other inclusions consisting of amyloidogenic proteins, such as neurofibrillary tangles or Lewy bodies (data not shown), indicating that NAB61 is specific for Aβ and does not recognize a pathologic conformation common to other amyloidogenic proteins.

Example 3

NAB61 Improves Spatial Learning and Memory

Figure 5A:
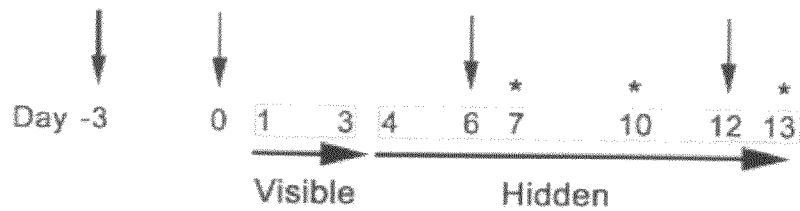
FIG. 5A is a schematic of the schedule of immunization and behavioral testing.

To probe the role of Aβ oligomers on cognitive dysfunction, 17-19 month old Tg2576 mice were immunized with NAB61 (n=14) or non-specific IgG (n=16) and tested in the MWM for spatial learning and memory, using the schedule shown in FIG. 5A. Non-transgenic mice were also treated with either IgG (n=7) or NAB61 (n=7). However, for statistical analysis, data from IgG and NAB61 treated non-transgenic control mice was pooled after performing a two-way ANOVA, which revealed no effect of treatment on performance in the hidden water maze for non-Tg mice (treatment, p=0.8974; block, p=0.0251; interaction, p=0.8942).

Figure 5B:
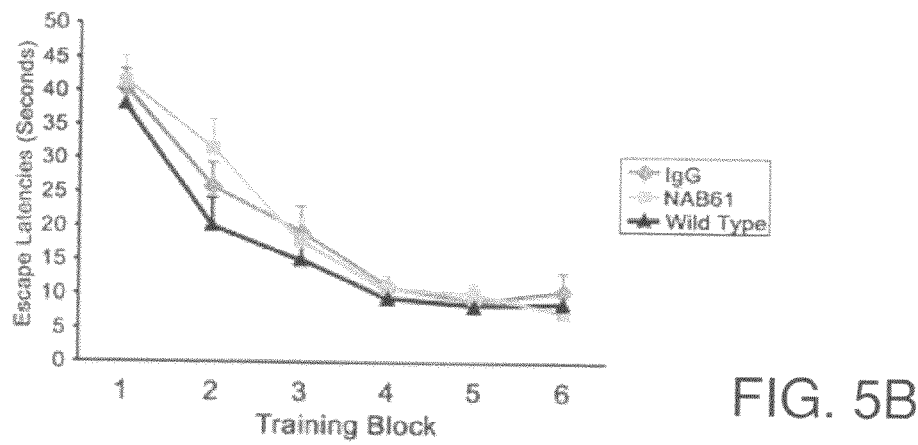
FIG. 5B is a graph of data from the performance in a visible water maze of NAB61-treated Tg2576, IgG-treated Tg2576 and non-transgenic wild-type mice.

To test for potentially confounding sensorimotor or motivational defects, latencies to reach a visible platform were measured over successive training blocks (4 trials/block). Non-transgenic, NAB61-treated Tg2576, and IgG-treated Tg2576 mice showed no deficits in the visible water maze (FIG. 5B). No significant differences were found between the three groups, indicating that motivational and sensorimotor functions were not affected either by genotype or by treatment. Although latencies for both NAB61-treated and IgG-treated Tg2576 mice on the second and third training blocks of the visible water maze tended to be higher than latencies for non-transgenic mice, differences in overall performance were insignificant (repeated measures ANOVA p=0.0814). Furthermore, the latency to reach the visible platform and swim speeds on both the first trial and the first block were not statistically different between the three groups (data not shown), indicative of the lack of confounding sensorimotor or motivational deficits.

Figure 5C:
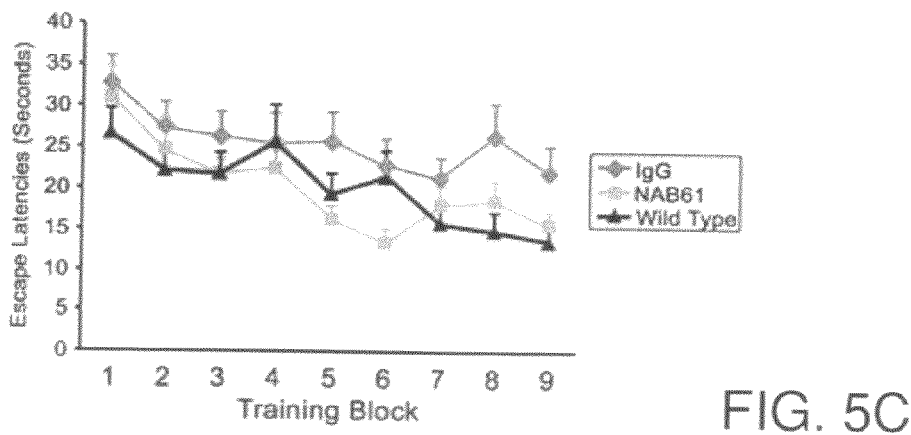
FIG. 5C is a graph of data from the performance in a hidden water maze of NAB61-treated Tg2576, IgG-treated Tg2576 and non-transgenic wild-type mice.

Spatial learning and memory were then tested using the hidden water maze in which the primary measure of learning and memory was latency to reach the hidden platform (FIG. 5C). IgG-treated Tg2576 mice showed no significant improvement in latencies over the testing period (one-way ANOVA, p=0.4402), whereas NAB61-treated Tg2576 mice and non-transgenic mice both showed a significant decrease in latency with training (one-way ANOVA: NAB61, p=0.0004; non-transgenic, p=0.0184). Furthermore, comparisons between the three groups of mice demonstrated that both non-transgenic and NAB61-treated Tg2576 mice performed significantly better than IgG-treated Tg2576 mice (repeated measures ANOVA, p=0.0002; non-transgenic vs. IgG, p=0.0014; NAB61 vs. IgG, p=0.0006). Therefore, passive immunization with NAB61 ameliorated behavioral deficits in the mice in the hidden water maze.

To confirm that the improved behavior on the hidden water maze was due to the acquisition of spatial reference memory, three probe trials were interpolated throughout the training process (FIG. 5A) in which the platform was removed, and the percentage of time spent searching in the target quadrant where the platform was usually located was determined. During the first probe trial, the three groups of mice exhibited spatially oriented swimming behavior, indicating that all three groups have acquired some degree of a spatial reference for the general location of the hidden platform (FIG. 5D). However, the time spent in the target quadrant relative to adjacent quadrants was only significantly different for NAB61-treated Tg2576 and non-transgenic mice. After further training, this behavioral measure became saturated and thus was unable to discern any differences between the three groups of mice in the final two probe trails (FIGS. 5E and 5F).

Figures 5G, 5H:
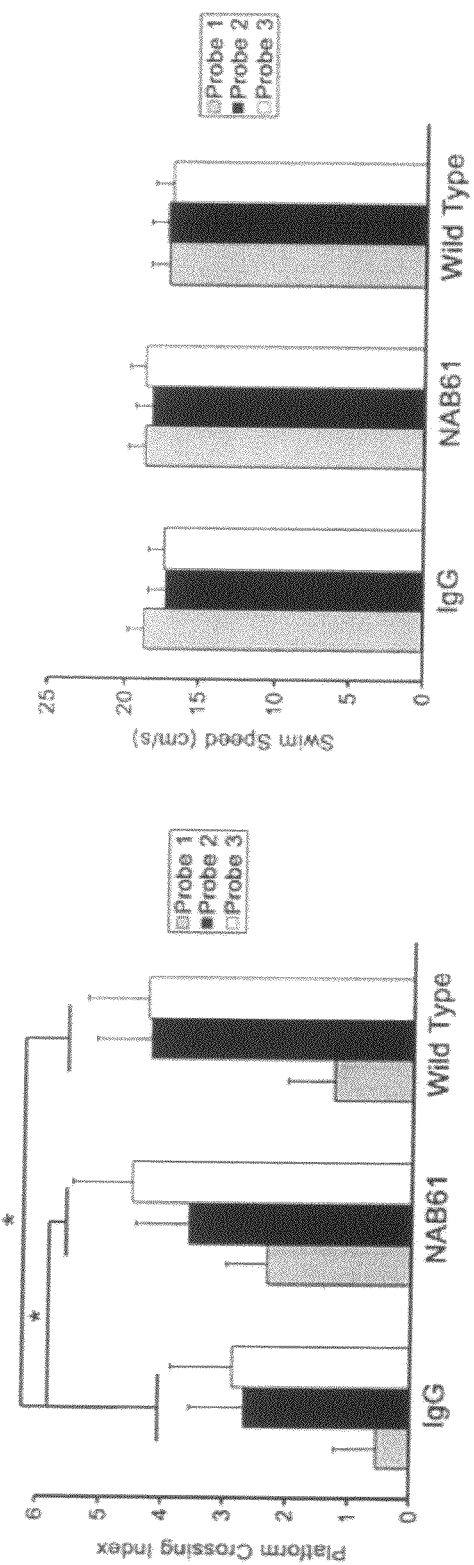
FIG. 5G depicts the results of spatial reference memory, in terms of a platform crossing index, for NAB61-treated Tg2576, IgG-treated Tg2576 and non-transgenic wild-type mice obtained during each probe trial. (* $p<0.05$)
FIG. 5H depicts the data for motor function in the Morris Water Maze for NAB61-treated Tg2576, IgG-treated Tg2576 and non-transgenic wild-type mice obtained during each probe trial.

Since the time spent by the mice in the target quadrant appeared to plateau by the second of the three probe trials, a third measure of spatial learning was used to confirm their improved acquisition of spatial reference memory following NAB61 immunization. A platform crossing index was calculated which measured the number of crossings over the exact location of the platform subtracted by the average number of crossings over the platform locations in non-target quadrants (FIG. 5G). Using this measure, both NAB61-treated Tg2576 mice and non-transgenic mice performed significantly better than IgG-treated Tg2576 mice (repeated measures ANOVA, p=0.0301; NAB61 vs. IgG, p=0.0332; non-transgenic vs. IgG, p=0.0426). Again, this effect was not due to the presence of motor deficits, since all three groups of mice exhibited similar swim speeds regardless of the probe trial (FIG. 5H; two-way ANOVA: group, p=0.4033; probe trial, p=0.8911; interaction, p=0.9804). Therefore, three independent statistical measures (latency, percent time in target quadrant, and platform crossing index) all indicated that short-term immunization with NAB61 improved spatial learning and memory in aged Tg2576 mice.

Example 5

NAB61 Immunization Does Not Affect APP Processing or Aβ Accumulation

Figure 6A:
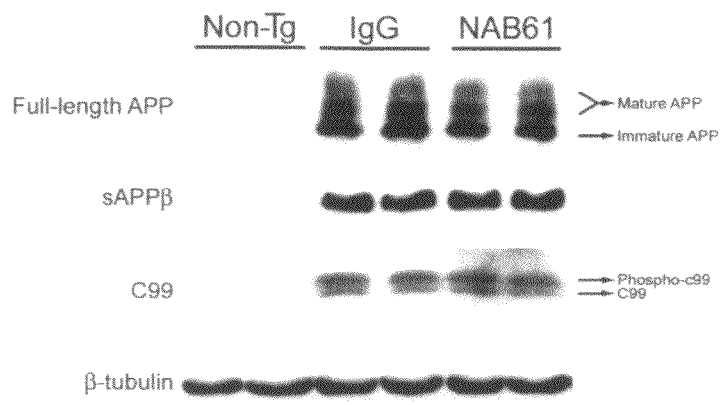
FIG. 6A depicts images of immunoblots of material immunoprecipitated from brain tissue of non-transgenic wild-type mice ("Non-tg"), IgG-treated Tg2576 and NAB61-treated Tg2576 mice after immunization treatment. Full-length APP was immunoprecipitated with a C-terminal APP antibody (5685) and immunoblotted with an N-terminal APP antibody (Karen). sAPPβswe levels were assessed by immunoblotting with an end-specific polyclonal antibody (54). C99 was immunoprecipitated with NAB228, run on a 10/16.5% Tris-tricine gel and immunoblotted with 5685. β-tubulin was immunoblotted with TUB2.1. "sAPPβswe" refers to a cleavage fragment of APPswe that is generated by one of the two cleavage events that ultimately release Aβ peptide.
Figure 6B:
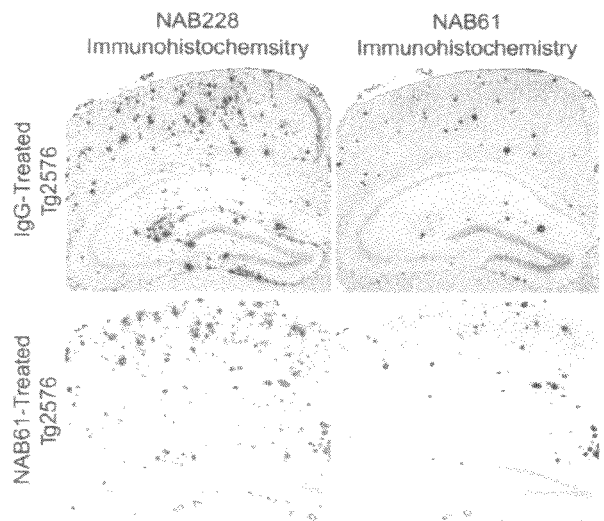
FIG. 6B is a series of images depicting serial sections of brain from Tg2576 mice treated with either non-specific IgG (top) or NAB61 (bottom) subjected to immunohistochemistry using either NAB228 (left) or NAB61 (right) as primary antibodies.
Figure 6D:
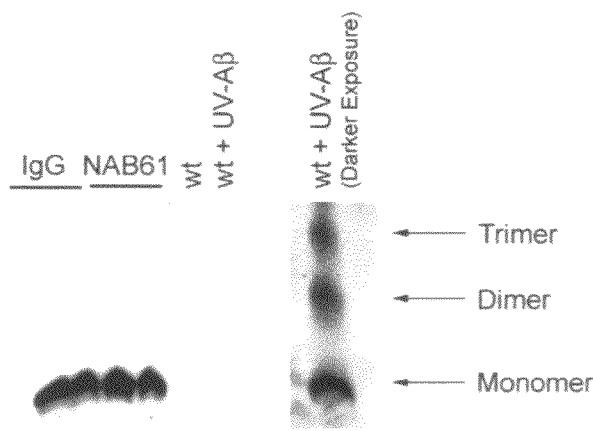
FIG. 6D is a series of images depicting immunoblots of immunoprecipitated plasma from Tg2576 mice treated with either non-specific IgG or NAB61 to examine peripheral Aβ Control lanes of untreated Aβ or UV-cross linked Aβ are on the right. A darker exposure of the UV-crosslinked Aβ lane is shown on the far right.
Figure 6C:
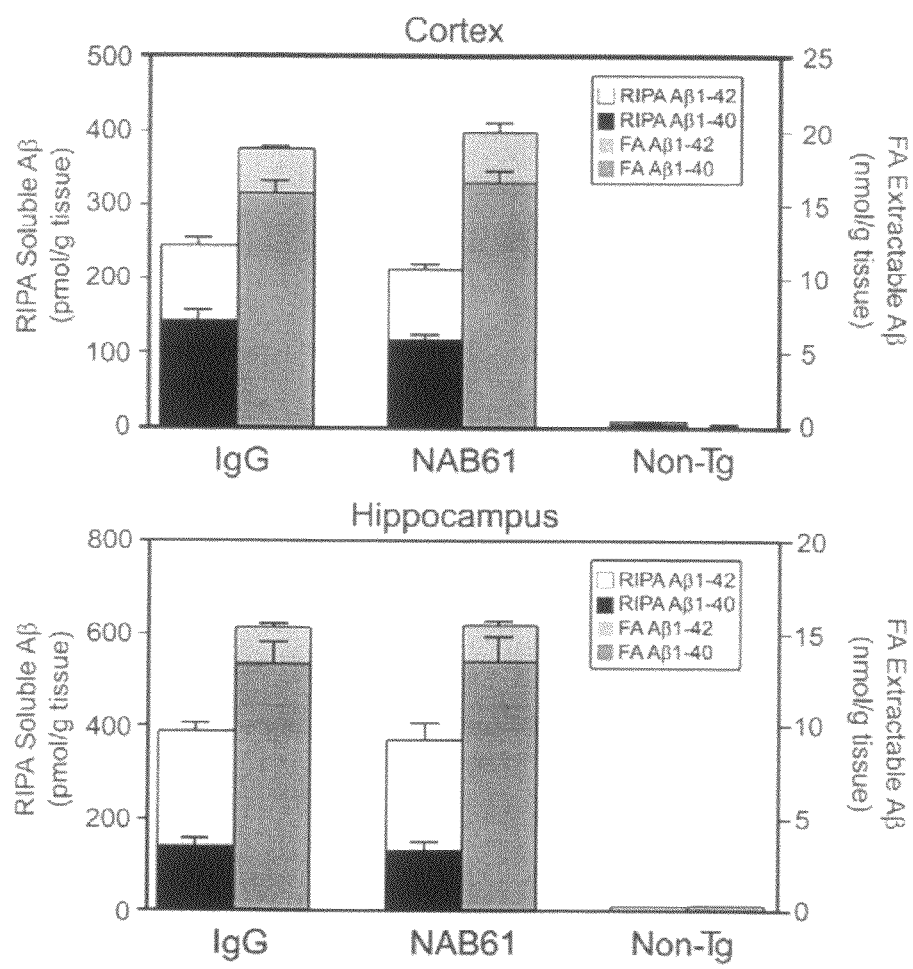
FIG. 6C is a series of graphs depicting the quantification of Aβ accumulation in cortical and hippocampal regions from Tg2576 mice treated with either non-specific IgG or NAB61. "Non-tg" refers to non-transgenic WT mice. Aβ concentrations were measured by sandwich ELISA specific for Aβ40 and Aβ42. FA=formic acid.

To demonstrate that the NAB61-mediated neutralization of Aβ oligomers was independent of effects on APP processing or the extent of Aβ amyloid pathology, the levels of APP and APP fragments in mice after NAB61 treatment was examined. Steady-state levels of full length APP, sAPPβ and C99 were not different among IgG-treated and NAB61-treated Tg2576 mice, arguing that NAB61 did not affect proteolytic processing of APP (FIG. 6A). Furthermore, no differences in amyloid plaque morphology, distribution or density were observed upon NAB228 or NAB61 immunohistochemistry (FIG. 6B). Additionally, quantification of detergent-soluble and insoluble levels of cortical and hippocampal Aβ by sandwich ELISA indicated that Aβ levels were not statistically different following short-term NAB61 immunization (FIG. 6C).

To further determine the effect of passive immunization on Aβ plaques, mice were subjected to 6 months of peripheral passive immunization with NAB61, after which Aβ levels were quantified using sandwich ELISAs, wherein JRF/c40 or JRF/c42 was the capture antibody and HRP-conjugated m266 was the reporter antibody (Table 1). Statistical analyses using two-tailed t-tests showed no significant differences between the two treatment groups. Thus, these data indicate that long term passive immunization with NAB61 does not reduce Aβ amyloid plaque burden.

NAB61 was not expected to affect peripheral pools of Aβ. Immunoprecipitation of Aβ from sera obtained from passively-immunized Tg2576 mice failed to demonstrate an increase in peripheral Aβ (FIG. 6D). Furthermore, naturally-occurring Aβ oligomers were not immunoprecipitated from sera samples, although very low concentrations of synthetic Aβ oligomers could be immunoprecipitated when added to sera samples (FIG. 6D). Having ruled out effects on APP processing, Aβ amyloid accumulation and peripheral pools of Aβ, the selectivity towards oligomeric Aβ exhibited by NAB61 suggested that direct neutralization of Aβ oligomers by immunization with NAB61 reversed learning and memory deficits in Tg2576 mice.

TABLE 1

| | Aβ40 (pmol/g) | | | Aβ42 (pmol/g) | | |
|---|---|---|---|---|---|---|
| | IgG | NAB61 | p-value | IgG | NAB61 | p-value |
| RIPA | | | | | | |
| Cortex | 25.3 ± 1.5 | 23.9 ± 0.9 | 0.43 | 6.9 ± 1.5 | 4.2 ± 0.5 | 0.08 |
| Hipp | 24.4 ± 1.0 | 22.8 ± 0.8 | 0.22 | 3.3 ± 0.2 | 8 ± 0.2 | 0.14 |
| FA | | | | | | |
| Cortex | 2830.7 ± 529.7 | 3170.8 ± 538.1 | 0.66 | 655.1 ± 94.3 | 864.6 ± 164.2 | 0.30 |
| Hipp | 1449.5 ± 221.8 | 1039.5 ± 172.2 | 0.16 | 449.6 ± 55.3 | 360.8 ± 60.0 | 0.30 |

Note:
Aβ levels are presented as average values ± standard error. "Hipp" is hippocampus. "FA" is formic acid.

Similarly, direct intracerebral inoculation in matched cohorts of Tg2576 mice did not reduce Aβ amyloid burden. The data from each individual mouse and a summary statistical analysis are shown in Tables 2 and 3, respectively. Although there was a trend towards lower Aβ amyloid burden after NAB61 injection, a one-sample two-tailed t-test indicated that the ratio of ipsilateral to contralateral Aβ amyloid burden was not significantly different from 1.000 for both IgG- and NAB61-injected mice. These data further demonstrate that the effect of NAB61 on cognitive behavior was via direct neutralization of Aβ oligomers, and not a result of APP processing or Aβ amyloid pathology.

TABLE 2

| Treatment | Age (mo) | Gender | Duration (d) | Amyloid burden (ipsi to contra ratio) |
|---|---|---|---|---|
| IgG | 8.7 | M | 3 | 1.09 |
| IgG | 10.8 | M | 7 | 1.37 |
| IgG | 9.2 | F | 7 | 1.15 |
| IgG | 9.8 | F | 7 | 0.96 |
| NAB61 | 8.0 | M | 3 | 0.90 |
| NAB61 | 10.8 | M | 7 | 1.14 |
| NAB61 | 10.9 | M | 7 | 1.11 |
| NAB61 | 11.1 | M | 7 | 0.76 |
| NAB61 | 9.2 | F | 7 | 0.79 |
| NAB61 | 9.2 | F | 7 | 0.81 |

TABLE 3

| Treatment | Mean | Std Error | Lower 95% CI | Upper 95% CI | P value |
|---|---|---|---|---|---|
| IgG | 1.143 | 0.066 | 0.958 | 1.327 | 0.098 |
| NAB61 | 0.918 | 0.068 | 0.743 | 1.094 | 0.285 |

Finally, passive immunization against Aβ has been thought to enhance the efflux of Aβ from the central nervous system into the periphery. However, the presence of Aβ oligomers has not been demonstrated in the periphery. Accordingly, The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. An isolated murine antibody that selectively binds to an epitope comprising residues 1-11 of human Aβ in an Aβ oligomer and does not recognize neurofibrillary tangles or Lewy bodies, wherein the antibody is monoclonal antibody NAB61.

2. The antibody of claim 1, wherein the Aβ oligomer is a dimer, trimer or tetramer.

3. The antibody of claim 1, wherein the Aβ oligomer is found in, or selected from, a mature senile plaque or a pathologic Aβ deposit.

4. A pharmaceutical composition, comprising an isolated murine antibody that selectively binds to an epitope comprising residues 1-11 of human Aβ in an Aβ oligomer and does not recognize neurofibrillary tangles or Lewy bodies, wherein the antibody is monoclonal antibody NAB61, and a pharmaceutical carrier.

5. The pharmaceutical composition of claim 4, wherein the Aβ oligomer is a dimer, trimer or tetramer.

6. The pharmaceutical composition of claim 4, wherein the Aβ oligomer is found in, or selected from, a mature senile plaque or a pathologic Aβ deposit.

7. A kit for selectively detecting an Aβ oligomer, the kit comprising an isolated murine antibody that selectively binds to an epitope formed by residues 1-11 of human Aβ in the Aβ oligomer and does not recognize neurofibrillary tangles or Lewy bodies, wherein the antibody is monoclonal antibody NAB61, and instructional material.

8. The kit of claim 7, wherein the Aβ oligomer is a dimer, trimer or tetramer.

9. An isolated antibody that selectively binds to an epitope comprising residues 1-11 of human Aβ in an Aβ oligomer and does not recognize neurofibrillary tangles or Lewy bodies, wherein the antibody is a humanized version of monoclonal antibody NAB61.

10. A pharmaceutical composition comprising the humanized antibody of claim 9.

11. A kit for selectively detecting an Aβ oligomer, the kit comprising the humanized antibody of claim 9, and instructional material.

12. A hybridoma cell line from which monoclonal antibody NAB61 is produced.

13. A method for treating a disease characterized by an amyloid deposit of Aβ in a patient, the method comprising administering to such patient in need thereof a therapeutically effective amount of an antibody that selectively binds to an epitope comprising residues 1-11 of Aβ in an Aβ oligomer and does not recognize neurofibrillary tangles or Lewy bodies, wherein the antibody is monoclonal antibody NAB61.

14. The method of claim 13, wherein the Aβ oligomer is a dimer, trimer or tetramer.

15. The method of claim 13, wherein the Aβ oligomer is found in, or selected from, a mature senile plaque or a pathologic Aβ deposit.

16. The method of claim 13, wherein the disease is Alzheimer's disease.

17. The method of claim 13, wherein the patient is human.

18. A method for treating a disease characterized by an amyloid deposit of Aβ in a patient, the method comprising administering to such patient in need thereof a therapeutically effective amount of an antibody that selectively binds to an epitope comprising residues 1-11 of Aβ in an Aβ oligomer and does not recognize neurofibrillary tangles or Lewy bodies, wherein the antibody is a humanized version of monoclonal antibody NAB61.

* * * * *